United States Patent [19]

Matsui et al.

[11] 3,947,519
[45] Mar. 30, 1976

[54] PREPARATION OF OPTICALLY ACTIVE ALLETHRORONE VIA ALLETHRONYL ACID PHTHALATE

[75] Inventors: Masanao Matsui, Tokyo; Fukashi Horiuchi, Kawanishi; Hajime Hirai; Nobushige Itaya, both of Nishinomiya, all of Japan

[73] Assignee: Sumitomo Chemical Company, Limited, Osaka, Japan

[22] Filed: Mar. 28, 1974

[21] Appl. No.: 455,725

[30] Foreign Application Priority Data

Mar. 29, 1973 Japan................................ 48-36473

[52] U.S. Cl. ...... 260/586 R; 260/475 A; 260/515 P
[51] Int. Cl.² ........................................ C07C 45/00
[58] Field of Search ........................ 260/586 R

[56] References Cited
UNITED STATES PATENTS
3,484,489   12/1969   Kierstead et al................ 260/586 R OTHER PUBLICATIONS
LaForge et al., "J. Am. Chem. Soc.", Vol. 74, pp. 5392–5394, (1952).

*Primary Examiner*—Norman Morgenstern
*Attorney, Agent, or Firm*—Wenderoth, Lind & Ponack

[57] ABSTRACT

The present invention relates to a process for preparing allethrolone which involves hydrolyzing 2-allyl-4-hydroxy-3-methyl-2-cyclopentenone acid phthalate represented by the formula

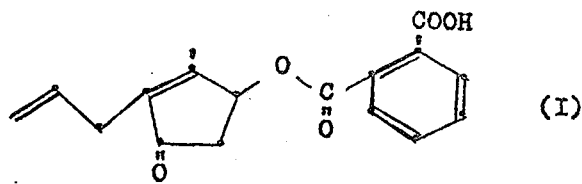

in water or an aqueous solvent with or without a base of less than a small excess of the equivalent.

9 Claims, No Drawings

PREPARATION OF OPTICALLY ACTIVE ALLETHRORONE VIA ALLETHRONYL ACID PHTHALATE

The present invention relates to a method for obtaining 2-allyl-4-hydroxy-3-methyl-2-cyclopentenone (referred to as allethrolone hereinafter).

More particularly, the present invention relates to a method for obtaining allethrolone characterized in that 2-allyl-4-hydroxy-3-methyl-2-cyclopentenone acid phthalate (referred to as allethronyl acid phthalate hereinafter) is hydrolyzed in water or in an aqueous solvent with or without a base of less than a small excess of the equivalent to the half-ester.

Hydrolysis of the optically active allethronyl acid phthalate affords optically active allethrolone, and hydrolysis of a racemic allethronyl acid phthalate affords a racemic allethrolone.

Allethrin (allethronyl chrysanthemate) has widely been used as a low toxic (to mammal) and rapidly effective insecticidal ester which has a similar chemical structure and insecticidal activity to natural pyrethrins. As allethrolone, an alcohol moiety of the allethrin, has an asymmetric carbon atom at the 4-position, it is present in two optical isomeric forms. Of the chrysanthemic acid esters of allethrolone, (+)-allethrolone ester is known to have several times greater insecticidal activity than (−)-allethrolone ester. It is, therefore, very important to develop a method for preparing optically active allethrolone industrially advantageously.

The only known method to prepare optically active allethrolone was based on optical resolution of the semi-carbazones of diastereoisomeric (±)-allethrolone-(+)-trans-chrysanthemates by means of fractional crystallization and cleavage of the separated semicarbazone into the optically active allethrolone (F. B. La Forge et al., J. Org. Chem., 19, 457, 1954).

This method, however, can not be applied industrially because it has such a number of difficulties as many reaction steps, complicated operation and low overall yield.

On the other hand, for optical resolution of a racemic alcohol, a method can most generally be carried out, which consists of resolution of the diastereoisomeric acid phthalates of the alcohol using an optically active amine, and hydrolysis of the resolved half-ester into the optically active alcohol.

La Forge et al., in their attempts to apply this method to the optical resolution of allethrolone, studied in details the hydrolysis of allethronyl acid phthalate which is an intermediate in the optically active allethrolone synthesis (F. B. La Forge et al., J. Am. Chem. Soc., 74, 5392, 1952). They showed that even at the room temperature the said phthalates could be hydrolized with an excess of caustic soda, i.e. 2,2-equivalents, to afford, no allethrolone at all, but only a dimeric product resulting from the condensation of two allethrolone molecules was obtained. From this fact, the optical resolution of allethrolone via its acid phthalate has been regarded as impossible. Furthermore, they described, at the beginning of the report, that allethrolone can not generally be regenerated on the hydrolysis of allethrolone carboxylic acid ester. The above-mentioned difficulty of recovery can also be understood sufficiently by the fact that pyrethrolone [2-(2'-4'-pentadienyl)-4-hydroxy-3-methyl-2-cyclopentenone] can not be obtained by the hydrolysis of the pyrethrin [(+)-pyrethronyl-(+)-trans-chrysanthemate], which has a very similar chemical structure to that of allethrin. So, to obtain pyrethrolone, Standinger and Ruzicka, who could not obtain pyrethrolone by the direct hydrolysis of pyrethrin, used a very troublesome process which consisted in the preparation of pyrethrin-semicarbazone, cleavage of the ester linkage by base-catalyzed ester exchange reaction and decomposition of pyrethrolone-semicarbazone to pyrethrolone with aqueous sodium bisulfate solution (H. Standinger and L. Ruzicka, Helv. Chim. Acta, 7, 177, 1924).

As can clearly be seen from the above examples, it has been believed almost impossible to obtain optically active allethrolone industrially.

The inventors, however, as a result of the long-term study found that the optically active allethronyl acid phthalate can be easily hydrolyzed in water or a water-containing solvent with or without a base of less than a small excess of the equivalent to afford optically active allethrolone. The molar ratio of the base to the allethronyl acid phthalate is from 0 to 1.2, and preferably from 0 to 1.0.

The (±)-allethronyl acid phthalate used as the starting material can be prepared according to the known method (La Forge et al., J. Am. Chem. Soc., 74, 5392, 1952) or by the reaction between allethrolone and phthalic anhydride in the presence of a tertiary amine such as triethylamine.

The hydrolysis of allethronyl acid phthalate unexpectedly proceeds very smoothly by heating in water or in an aqueous solvent, and allethrolone can be regenerated in a good yield. If necessary, the hydrolysis can be accelerated by the addition of a suitable amount of a base.

In this process if optically active allethronyl acid phthalate is used as the starting material, optically active allethrolone can be obtained without racemization.

The above-mentioned reaction process can be represented by the following schema:

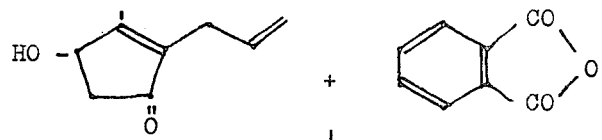

La Forge et al., J. Am. Chem. Soc., 74, 5392 (1952).

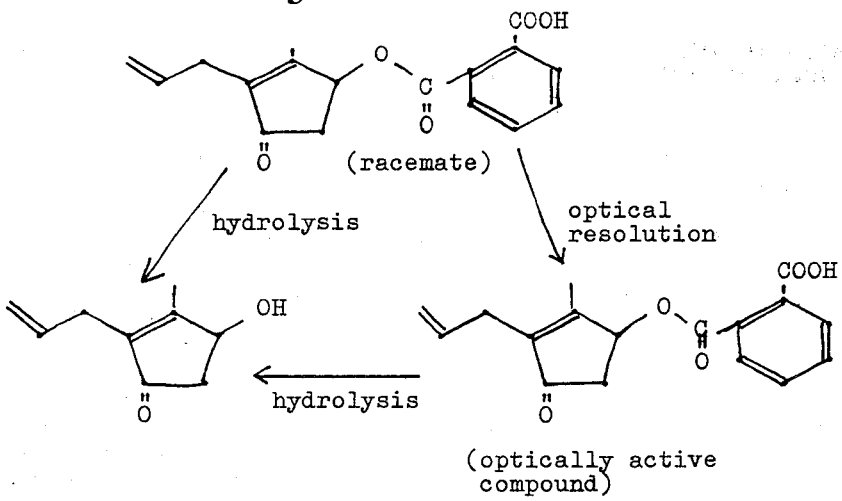

(optically active compound)

Though it can easily be seen from the Examples that the presence of a base is not essential for the practice of the present invention, an addition of a base is preferred to accelerate the rate of hydrolysis. In this case, it is very important that the amount of base to be added is limited preferably to not more than an equivalent of allethronyl acid phthalate. Though small excess is also permissible, the use of base in a large excess (over 1.2 equivalent) results in rapid formation of the dimeric allethrolone which was described by La Forge et al., and no allethrolone can be obtained.

According to the present invention, the hydrolysis of allethronyl acid phthalate is carried out in a solvent at a temperature from room temperature to 250° C. for several minutes to 100 hours. If necessary, to accelerate the reaction, the hydrolysis can be carried under elevated pressure, with the addition of a base in a small excess of an equivalent to allethronyl acid phthalate, or with the addition of a surfactant. The solvents which can be used include water, and water-miscible solvents such as methanol, ethanol, glycerin, ethyleneglycol, diethyleneglycol, triethyleneglycol, acetone, tetrahydrofuran, dioxane, dimethylsulfoxide and dimethylformamide. For protection of the allethrolone from undesirable side reaction the reaction can be run in an aqueous solvent with water-immiscible solvents such as ether, benzene, toluene, xylene, dichloromethane, chloroform, carbon tetrachloride, dichloroethane, petroleum ether, petroleum benzin, ligroin, n-hexane, 1-butanol, 2-butanol, tert.-butanol, and methylethylketone. For the same purpose the reaction can be carried out in a buffer which enables the reaction system to be kept at near the neutral state.

Not particularly limited, the base which can be used is chosen from alkali metal or alkali earth metal hydroxides oxides, carbonates, bicarbonates, phosphates, cyanides, sulfides, borates, formates, acetates, propionates or benzoates; and amines (including ammonia), such as methylamine, dimethylamine, trimethylamine, ethylamine, diethylamine, triethylamine, cyclohexylamine, dicyclohexylamine, N-methylcyclohexylamine, N,N-dimethylcyclohexylamine, pyrrolidine, N-methylpyrrolidine, piperidine, N-methylpiperidine, morphorine, N-methylmorphorine, aniline, N-methylaniline, N-ethylaniline, N,N-dimethylaniline, N,N-diethylaniline, benzylamine, N-methylbenzylamine, N,N-dimethylbenzylamine, pyridine, quinoline, isoquinoline, and α-, β- and γ-picoline. These bases can be used as a mixture. Needless to say, alkali metal, alkali earth metal, ammonium or amine salt of allethronyl acid phthalate may be used for hydrolysis.

In addition, the resolved, optically active diastereoisomeric salt can be hydrolysed without isolating optically active allethronyl acid phthalate.

After the hydrolysis the reaction mixture is basified, if necessary, and saturated with sodium chloride, urea or sodium sulfate and is extracted with an organic solvent such as ether benzene or toluene.

The separated organic layer, after washing with a saturated aqueous sodium chloride, is dried and concentrated under a reduced pressure to give pure allethrolone. When hydrolysed mixture is first acidified, oily allethrolone and crystalline phthalic acid are deposited at the same time. In this case, the mixture is triturated with an organic solvent and filtered, and the separated organic layer is treated in the same way as above mentioned.

The present invention is further illustrated by the following non-limitative examples.

EXAMPLE 1

3.00 g. of (±)-allethronyl acid phthalate was heated in 10.0 g. of boiling water for 20 hours under vigorous stirring. The reaction mixture was cooled to a room temperature and saturated with sodium chloride, and extracted twice with ether. The ether solution was washed with a saturated aqueous sodium chloride solution, dried over anhydrous magnesium sulfate and concentrated under a reduced pressure to give 1.47 g. of a pale yellow oil. If crystal was separated in the oil, the mixture was triturated with chloroform, filtered and concentrated. The oil, purified by vacuum distillation (b.p. 109° – 110° C./0.3 mm.), was found to be almost pure (±)-allethrolone on NMR, IR and gas chromatography.

Yield 1.38 g.

EXAMPLE 2

The mixture of 3.00 g. of (±)-allethronyl acid phthalte, 10.0 g. of water and 0.6 g. of sodium chloride was heated at 100°C. for 17 hours under vigorous stirring, and then treated in nearly the same manner as described in Example 1 to give 1.45 g. of (±)-allethrolone.

EXAMPLE 3

3.00 g. of (±)-allethronyl acid phthalate, 10.0 g. of water and 0.80 g. of sodium bicarbonate were heated at 100°C. for 6 hours, and then treated in nearly the same manner as described in Example 1 to give 1.27 g. of (±)-allethrolone.

EXAMPLE 4

3.0 g. of (±)-allethronyl acid phthalate, 10.0 g. of water and 0.42 g. of sodium bicarbonate were heated at 100°C. for 8 hours, and then treated in nearly the same manner as described in Example 1 to give 1.46 g. of (±)-allethrolone.

EXAMPLE 5

3.0 g. of (±)-allethronyl acid phthalate, 10.0 g. of water and 0.04 g. of sodium bicarbonate were heated at 100°C. for 10 hours, and then treated in nearly the same manner as described in Example 1 to give 1.48 g. of (±)-allethrolone.

EXAMPLE 6

3.0 g. of (±)-allethronyl acid phthalate, 10.0 g. of water and 0.7 g. of disodium, phosphate were heated at 100°C. for 6 hours, and then treated in nearly the same manner as described in Example 1 to give 1.35 g. of (±)-allethrolone.

EXAMPLE 7

3.0 g. of (±)-allethronyl acid phthalate, 10.0 g. of water and 0.60 g. of a 28% aqueous ammonia were heated at 100°C. for 8 hours, and then treated in nearly the same manner as described in Example 1 to give 1.40 g. of (±)-allethrolone.

EXAMPLE 8

3.0 g. of (±)-allethronyl acid phthalate, 10.0 g. of water and 1.03 g. of a 30% methylamine solution were heated at 100°C. for 6 hours, and then treated in nearly the same manner as described in Example 1 to give 1.41 g. of (±)-allethrolone.

EXAMPLE 9

3.0 g. of (±)-allethronyl acid phthalate, 10.0 g. of water and 1.13 g. of a 40% aqueous dimethylamine were heated at 100°C. for 7 hours, and then treated in nearly the same manner as described in Example 1 to give 1.32 g. of (±)-allethrolone.

EXAMPLE 10

3.0 g. of (±)-allethronyl acid phthalate, 10.0 g. of water and 1.00 g. of triethylamine were heated at 100°C. for 8 hours, and then treated in nearly the same manner as described in Example 1 to give 1.40 g. of (±)-allethrolone.

EXAMPLE 11

12.80 g. of (−)-allethronyl acid phthalate ($[\alpha]_D^{22}$ −45.9° (in ethanol)), 50.0 g. of water and 3.23 g. of sodium bicarbonate were heated at 100°C. for 6 hours, and then treated in nearly the same manner as described in Example 1 to give 5.40 g. of optically active allethrolone; $[\alpha]_D^{22}$ +6.5° (in ethanol).

Optically active (−)-allethronyl acid phthalate is prepared, for example, as follows: Thus, to the solution of 16.0 g. of (±)-allethronyl acid phthalate and 6.4 g. of (+)-α-phenylamine in 55 g. of benzene, was added 18 g. of n-hexane. After standing at room temperature, the precipitates were filtered to obtain 8.0 g. of a crude salt (m.p. 111° − 113°C.)

The salt was recrystallized from the same solvent to give 6.0 g. of white crystals; m.p. 115° − 116°C., $[\alpha]_D^{22}$ −17.8° (in ethanol). The purified salt was added into a cold 2% aqueous sodium bicarbonate solution and separated free (+)-α-phenylethylamine was extracted with benzene. The aqueous layer was made acidic with conc. hydrochloric acid, and the resulting oil was extracted with ether. The ether layer was washed with water, dried over anhydrous magnesium sulfate, and concentrated under a reduced pressure to give 4.1 g. of (−)-allethronyl acid phthalate as a very viscous, oil; $[\alpha]_D^{22}$ −45.9° (in ethanol).

EXAMPLE 12

9.7 g. of (+)-allethronyl acid phthalate ($[\alpha]_D^{22}$ +48.7° (in ethanol)), 50.0 g. of water and 1.37 g. of sodium bicarbonate were heated at 100°C. for 10 hours, and then treated in nearly the same manner as described in Example 1 to give 4.5 g. of optically active allethrolone; $[\alpha]_D^{22}$ −6.8° (in ethanol).

Optically active (+)-allethronyl acid phthalate is prepared, for example, as follows. Thus, to a hot solution of 18.0 g. of (±)-allethronyl acid phthalate and 10.3 g. of (−)-α-(2-naphthyl)-ethylamine in a mixed solvent of 80.0 g. of toluene and 30.0 g. of n-hexane, was allowed to cool to a room temperature. The precipitates were filtered thoroughly washed with the above mixed solvent, and dried in a desiccator to give 6.50 g. of colorless crystal; m.p. 113° − 115°C., $[\alpha]_D^{22}$ +9.93° (in ethanol).

The salt was cleaved with 1% hydrochloric acid and separated free (+)-allethronyl acid phthalate was extracted with ether. The ether layer was washed with water, dried over anhydrous magnesium sulfate and concentrated under a reduced pressure to give 4.10 g. of (+)-allethronyl acid phthalate as a very viscous oil; $[\alpha]_D^{22}$ +41.7° (in ethanol).

EXAMPLE 13

21.0 g. of (−)-allethronyl acid phthalate ($[\alpha]_D^{21}$ −44.58° (in ethanol)), 70 g. of water and 7.90 g. of 40% aqueous dimethylamine were heated at 100°C. for 7 hours, and then treated in nearly the same manner as described in Example 7 to give 9.15 g. of optically active allethrolone; $[\alpha]_D^{21}$ +6.57° (in ethanol).

EXAMPLE 14

17.1 g. of (−)-allethronyl acid phthalate ($[\alpha]_D^{21}$ −44.58° (in ethanol)), 57 g. of water and 3.5 g. of a 28% aqueous ammonia were heated at 100°C. for 8 hours, and then treated in nearly the same manner as described in Example 7 to give 8.0 g. of optically active allethrolone; $[\alpha]_D^{21}$ +6.52° (in ethanol).

What is claimed is:

1. A method for preparing allethrolone, which comprises hydrolyzing 2-allyl-4-hydroxy-3-methyl-2-cyclopentenone acid phthalate represented by the formula

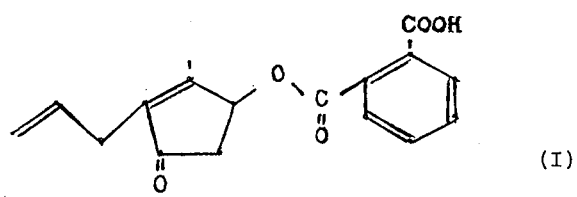

(I)

in water or an aqueous solvent consisting of water and a solvent selected from the group consisting of methanol, ethanol, glycerine, ethyleneglycol, diethyleneglycol, triethyleneglycol, acetate, tetrahydrofuran, dioxane, dimethylsulfoxide and dimethylformamide with or without a base of less than a small excess of the equivalent, said base being selected from the group consisting of alkali metal and alkali earth metal hydroxides, carbonates, bicarbonates, phosphates, cyanides, sulfides, borates, formates, acetates, propionates and benzoates, and amines and mixtures thereof.

2. A method according to claim 1, wherein the starting material is the optically active allethronyl acid phthalate.

3. A method according to claim 1, wherein the reaction is carried out in the presence of base and in the presence of a solvent at from room temperature to 250°C.

4. A method according to claim 3, wherein the molar ratio of the base to the allethronyl acid phthalate is 0 to 1.2.

5. A method according to claim 1, wherein the hydrolysis takes place in the presence of water.

6. A method according to claim 5, wherein the hydrolysis takes place in the presence of water and a base.

7. A method according to claim 1, wherein the hydrolysis takes place in the presence of an aqueous solvent and a base.

8. A method according to claim 1, wherein the hydrolysis takes place in the presence of water or an aqueous solvent without the presence of a base.

9. A method according to claim 1, wherein the hydrolysis is carried out at a temperature of from room temperature to 250°C for several minutes to 100 hours.

* * * * *